United States Patent
Cao et al.

(10) Patent No.: US 7,285,781 B2
(45) Date of Patent: Oct. 23, 2007

(54) CHARACTERIZING RESIST LINE SHRINKAGE DUE TO CD-SEM INSPECTION

(75) Inventors: Gary X. Cao, Santa Clara, CA (US); George Chen, Los Gatos, CA (US); Brandon L. Ward, San Jose, CA (US); Nancy J. Wheeler, Mountain View, CA (US); Alan Wong, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 644 days.

(21) Appl. No.: 10/886,387

(22) Filed: Jul. 7, 2004

(65) Prior Publication Data

US 2006/0006328 A1    Jan. 12, 2006

(51) Int. Cl.
*G01N 23/00* (2006.01)
*G03F 7/20* (2006.01)
*G03F 7/00* (2006.01)
*G03F 7/40* (2006.01)

(52) U.S. Cl. .................. 250/311; 250/306; 250/307; 250/310; 250/492.22; 250/492.3; 430/310; 430/313; 430/314; 430/317; 430/323; 356/634; 356/635; 356/636; 438/8; 438/16; 438/584

(58) Field of Classification Search .............. 250/311; 430/310
See application file for complete search history.

(56) References Cited

U.S. PATENT DOCUMENTS

| | | | |
|---|---|---|---|
| 6,319,655 B1 * | 11/2001 | Wong et al. ................. 430/311 |
| 6,541,182 B1 * | 4/2003 | Louis Joseph Dogue et al. 430/296 |
| 6,730,458 B1 * | 5/2004 | Kim et al. ................... 430/296 |
| 6,753,129 B2 * | 6/2004 | Livesay et al. ............. 430/296 |
| 6,774,044 B2 * | 8/2004 | Ke et al. ..................... 438/706 |
| 6,833,221 B2 * | 12/2004 | McArthur et al. ............. 430/5 |
| 7,064,846 B1 * | 6/2006 | Amblard et al. ............ 356/636 |
| 2003/0022072 A1 * | 1/2003 | Campi et al. .................. 430/5 |
| 2003/0224252 A1 * | 12/2003 | Zhou et al. .................... 430/5 |
| 2004/0152024 A1 * | 8/2004 | Livesay et al. ............. 430/394 |
| 2005/0023463 A1 * | 2/2005 | Ke et al. ..................... 250/307 |
| 2006/0006328 A1 * | 1/2006 | Cao et al. .................... 250/310 |
| 2006/0154181 A1 * | 7/2006 | Hada et al. ................. 430/322 |

* cited by examiner

*Primary Examiner*—Jack I. Berman
*Assistant Examiner*—Bernard Souw
(74) *Attorney, Agent, or Firm*—Fish & Richardson P.C.

(57) ABSTRACT

A CD-SEM (critical dimension-scanning electron microscope) system may utilize a technique for characterizing and reducing shrinkage carryover due to CD-SEM measurements. The system may identify the affects of CD-SEM measurements on the resist and adjust the operating parameters for a particular resist to avoid or significantly reduce shrinkage carryover. In this manner, the system may obtain more reliable CD measurements and avoid damage to the measured feature.

39 Claims, 9 Drawing Sheets

CHARACTERIZING RESIST LINE SHRINKAGE DUE TO CD-SEM INSPECTION

BACKGROUND

Scanning Electron Microscopes (SEMS) may be used by semiconductor device manufacturers to measure the "critical dimension" (CD) of the sub-micron-sized circuits in a chip in order to monitor the accuracy of their manufacturing process. CD measurements are typically performed after photolithographic patterning and subsequent etch processing.

An SEM uses a beam of electrons which is shaped and focused by magnetic and electrostatic "lenses" within an electron column. This beam causes secondary electrons and backscattered electrons to be released from the wafer surface. The SEM may then analyze the collected electrons (mainly the secondary electrons) to extract information, e.g., an image or measurement. The use of extremely precise and narrow electron beams may enable SEMs to image and measure features on a semiconductor wafer at a much higher resolution than images captured by optical microscopes.

DETAILED DESCRIPTION

Figure 1:
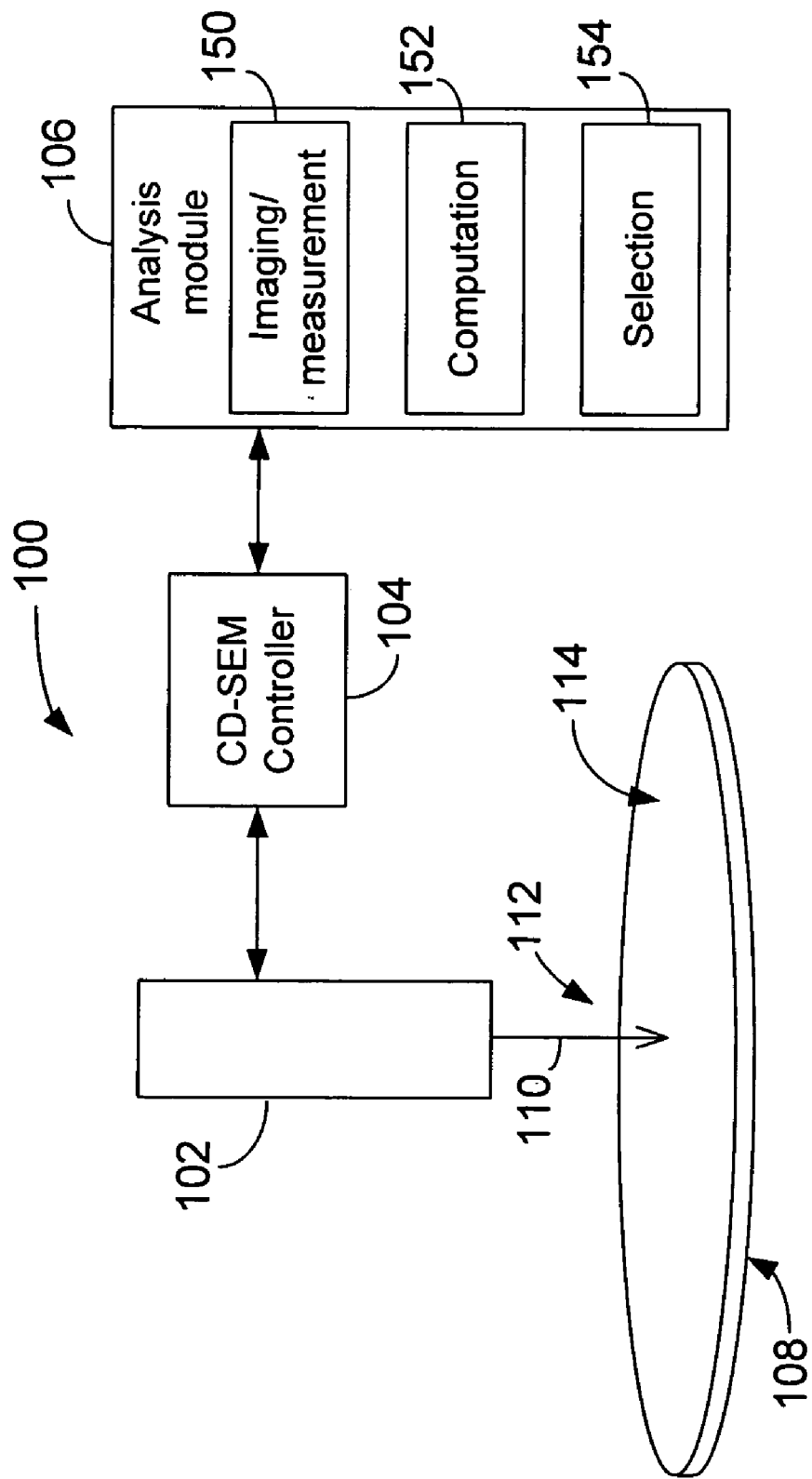
FIG. 1 is a block diagram of a CD-SEM (Critical Dimension-Scanning Electron Microscope) system.

FIG. 1 shows a CD-SEM (Critical Dimension-Scanning Electron Microscope) system 100 according to an embodiment. The system may include a CD-SEM 102, a CD-SEM controller 104 to control the operation and operating parameters of the CD-SEM 102, and an analysis module 106 to analyze the data collected by the CD-SEM.

The CD-SEM system 100 may be used to measure the CD of features in devices on a wafer 108 in order to monitor the accuracy of the manufacturing process. The CD measurements may be performed after photolithographic patterning and subsequent etch processing, e.g., on the patterned resist layer prior to etching the substrate and also on the etched layer.

The CD-SEM 102 produces a beam 110 of electrons, which is shaped and focused by magnetic and electrostatic "lenses" within an electron column. The beam causes secondary electrons and backscattered electrons 112 to be released from the wafer surface 114, which may be collected by the CD-SEM. The analysis module 106 may include an imaging/measurement module 150 to generate an image or measurement from information obtained from the collected secondary electrons.

The photoresist material used in a lithography process may be specific to the wavelength of light used in the lithography system. For example, 193 nm resist materials may be used in a lithography system using 193 nm UV light to expose the mask pattern onto the wafer. Next generation lithography system may use sub-193 nm wavelengths, e.g., 126 nm and 157 nm wavelengths generated by argon excimer and fluorine lasers, respectively. The sensitivity of these resist materials may be such that they are affected by the CD-SEM electron beam 110 used to measure features in the patterned photoresist layer.

Figure 2A:
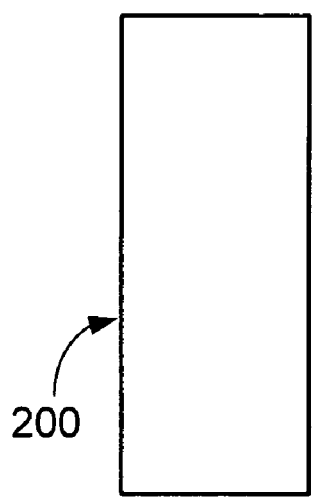
FIG. 2A is a plan view of a resist line before a CD-SEM measurement at an initial condition.
Figure 2B:
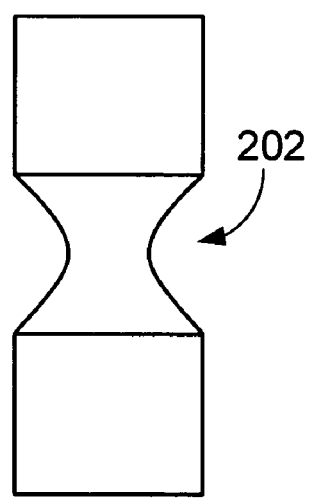
FIG. 2B is a plan view of the resist line of FIG. 2A after a CD-SEM measurement at the initial condition.
Figure 2C:
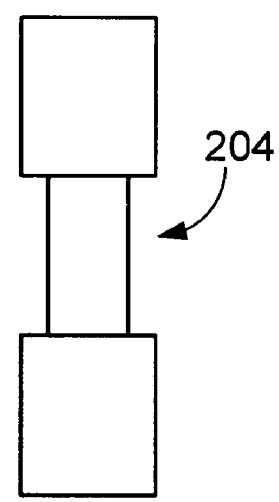
FIG. 2C is a plan view of a line in the substrate after etching the resist line of FIG. 2B.

FIGS. 2A-2C show the affect of the CD-SEM measurement on a line 200 of 193 nm resist. FIG. 2A shows the line before the measurement by the CD-SEM 102. FIG. 2B shows that the middle of the line 202 is severely shrunk after measurement with the CD-SEM. This shrinkage may be, a physical effect such as a thermal effect, a chemical effect involving changes in bond structure and atomic group re-arrangement, or a combination of both. Because the line shrinkage occurs during measurement, determining the true CD line value from the obtained CD-SEM measurement may be extremely difficult.

Figure 3A:
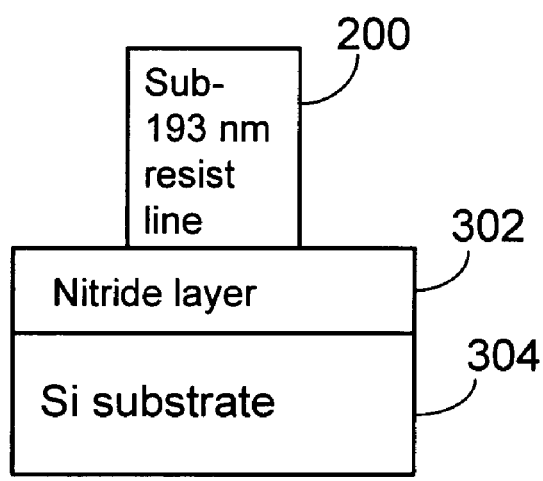
FIG. 3A is a sectional view of the resist line of FIG. 2A.
Figure 3B:
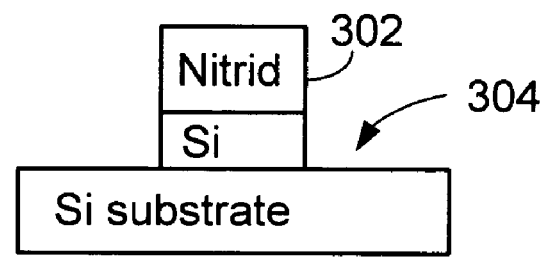
FIG. 3B is a sectional view of the feature line of FIG. 2C.

FIG. 3A is a sectional view showing the resist line 200 prior to etching. During etching, the photoresist is removed, and the nitride layer 302 and a portion of the substrate 304 may be etched, thereby transferring the pattern in the photoresist layer to the semiconductor device layers (e.g., nitride and silicon substrate). FIG. 2C shows the result of the shrinkage in the photoresist line due to the CD-SEM measurement after etching. The shrunk section 202 in the resist line 200 may result in a thinned portion 204 in the etched line in the device layers. While CD measurements may typically be performed in the scribe line between die (non-device) regions on the wafer, in some cases, it may be necessary to perform CD measurements in the device. The shrinkage carryover, or "fingerprint", from the CD-SEM measurement of the resist line may affect the performance of the device. Thus, CD-SEM measurements may not only be inaccurate, they may adversely affect yield.

In an embodiment, the affects of CD-SEM measurements on the resist may be identified, and the operating parameters adjusted for a particular resist to avoid or significantly reduce shrinkage carryover in order to obtain more reliable CD measurements and avoid damage to the measured feature.

Figure 4:
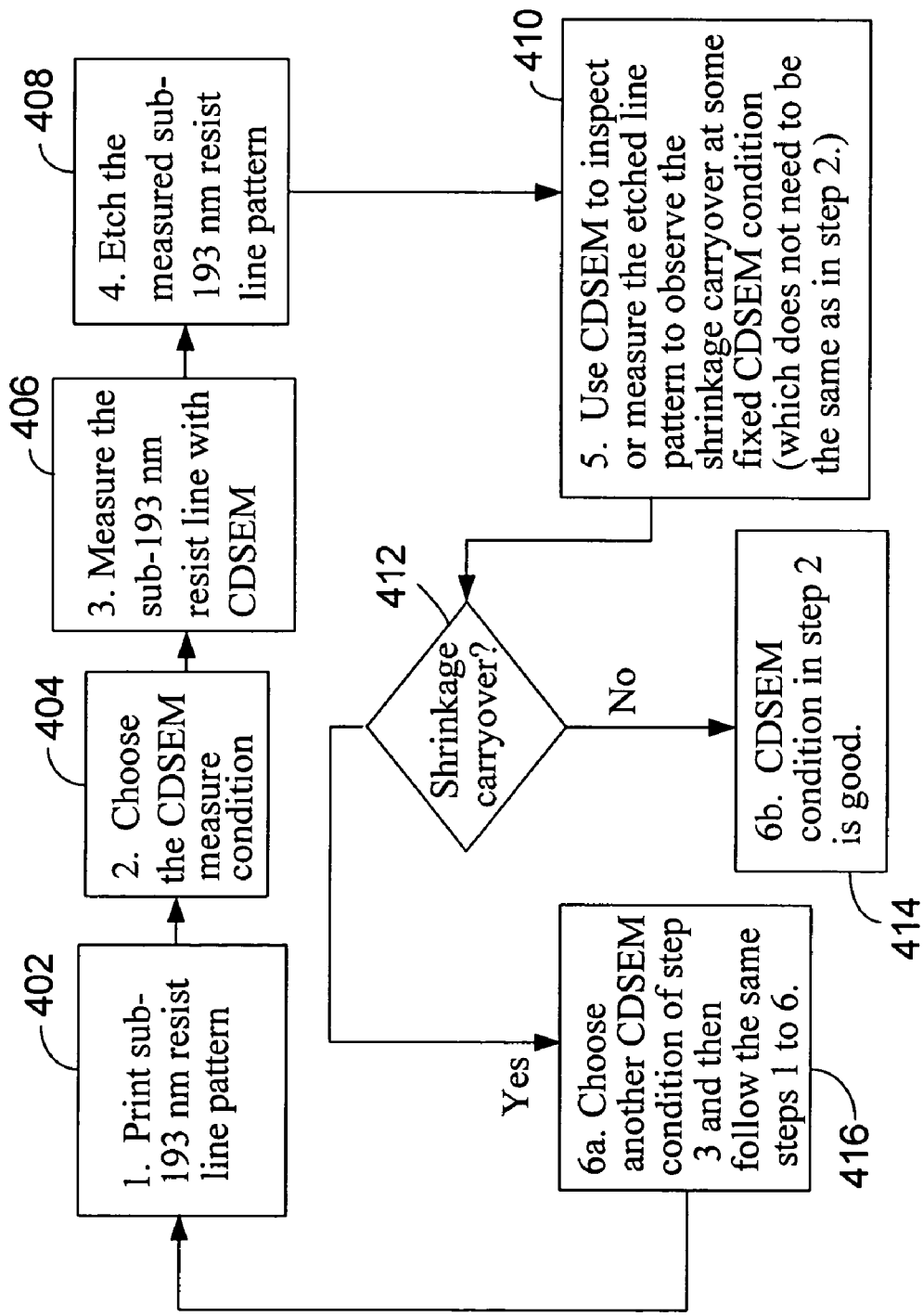
FIG. 4 is a flowchart describing a technique for characterizing and reducing shrinkage carryover due to CD-SEM measurements.

FIG. 4 is a flowchart describing a technique for characterizing and reducing shrinkage carryover due to CD-SEM measurements. A resist line pattern may be printed on the wafer (block 402). A CD-SEM condition may then be selected (block 404). The condition may be a set of operating parameters. The operating parameters for a CD-SEM measurement may include, for example, beam voltage, probe current, dose of electron energy, focusing method, image scanning frames, etc. A resist line in the pattern may then be measured with the electron beam with the selected parameters (block 406). The measured resist line (and the rest of the patterned resist layer) may be etched to produce features in the wafer (block 408). The CD-SEM may then be used again to measure the etched line pattern to observe any shrinkage carryover at some fixed CD-SEM condition (block 410). Measurements may be taken of the measured location and an unmeasured location. The shrinkage carryover may be calculated by a computation module 152 from the two measurements. Also, the shrinkage carryover may manifest itself as a slimming of a resist line, or conversely, enlargement of negative feature, such as a hole (e.g., via) or space, by slimming of the resist edges surrounding the negative feature.

Figure 5A:
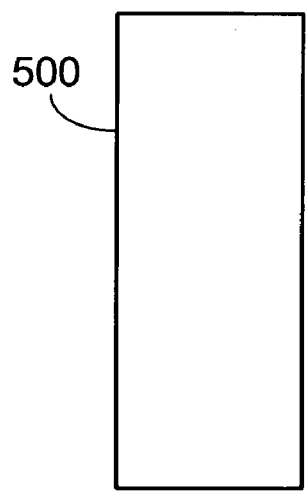
FIG. 5A is a plan view of a resist line before a CD-SEM measurement at a modified condition.
Figure 5B:
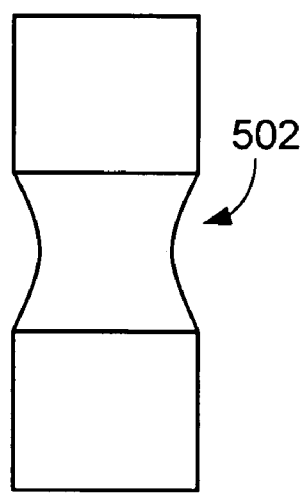
FIG. 5B is a plan view of the resist line of FIG. 5A after a CD-SEM measurement at the modified condition.
Figure 5C:
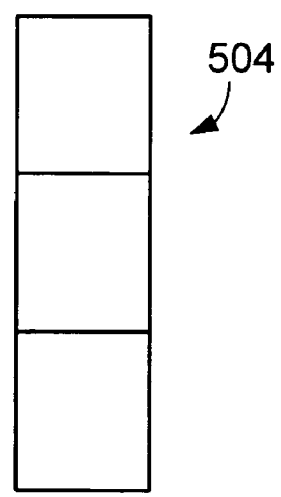
FIG. 5C is a plan view of a line in the substrate after etching the resist line of FIG. 5B.

The CD-SEM condition for the second measurement may not necessarily have to be the same as that in block 406 because the etched feature in the device layers may not be as susceptible to damage as the photoresist material. Consequently, the second measurement may be more accurate and non-damaging. The results of the measurement may then be analyzed by the analysis module 106 for evidence of shrinkage carryover (block 412). If no shrinkage carryover is discovered (or it falls below a threshold) (block 414), the condition used to measure in block 406 may be deemed satisfactory for the particular resist material under testing. This condition is shown in FIGS. 5A-5C, where the unshrunk resist line 500 (FIG. 5A) is lightly shrunk 502 after CD measurement (FIG. 5B) and then etched, resulting in a line 504 with no (or below threshold) shrinkage carryover (FIG. 5C). However, if shrinkage carryover (over a certain threshold) is observed (block 416), a new condition may be selected by a selection module 154 in the analysis module 106. The threshold may be based on an amount of shrinkage that is tolerable without causing device failure or malfunction, and in terms of change in width (CD) this may be about 1% of the feature size, depending on the processes and technologies. For example, a width change of 1/10 (or 10 nm) for a feature size of 100 nm may be unacceptable, whereas a width change of 1/50 (or 2% or 2 nm) of the feature size of 100 nm may be acceptable. On the other hand, for a larger feature size of 1000 nm, the shrinkage carryover may not tolerate a threshold value as small as 2% which is 20 nm. Thus the threshold may be selected based on the line (feature) dimension (CD) range. This is because shrinkage carryover may not be a linear function of feature size. For example, for a CD range of 100-200 nm features, the shrinkage carryover amount may be between 10% and 15%, corresponding to values of 10 nm to 30 nm. However, for larger CDs, e.g., in the 1000 nm (1.0 micron) range, a 30 nm shrinkage carryover is a much smaller value in percentage, e.g., about 3%.

Another resist layer may be printed and blocks 404-412 repeated with new CD-SEM condition(s) until a satisfactory CD-SEM condition is determined for the resist material under consideration.

Figure 6:
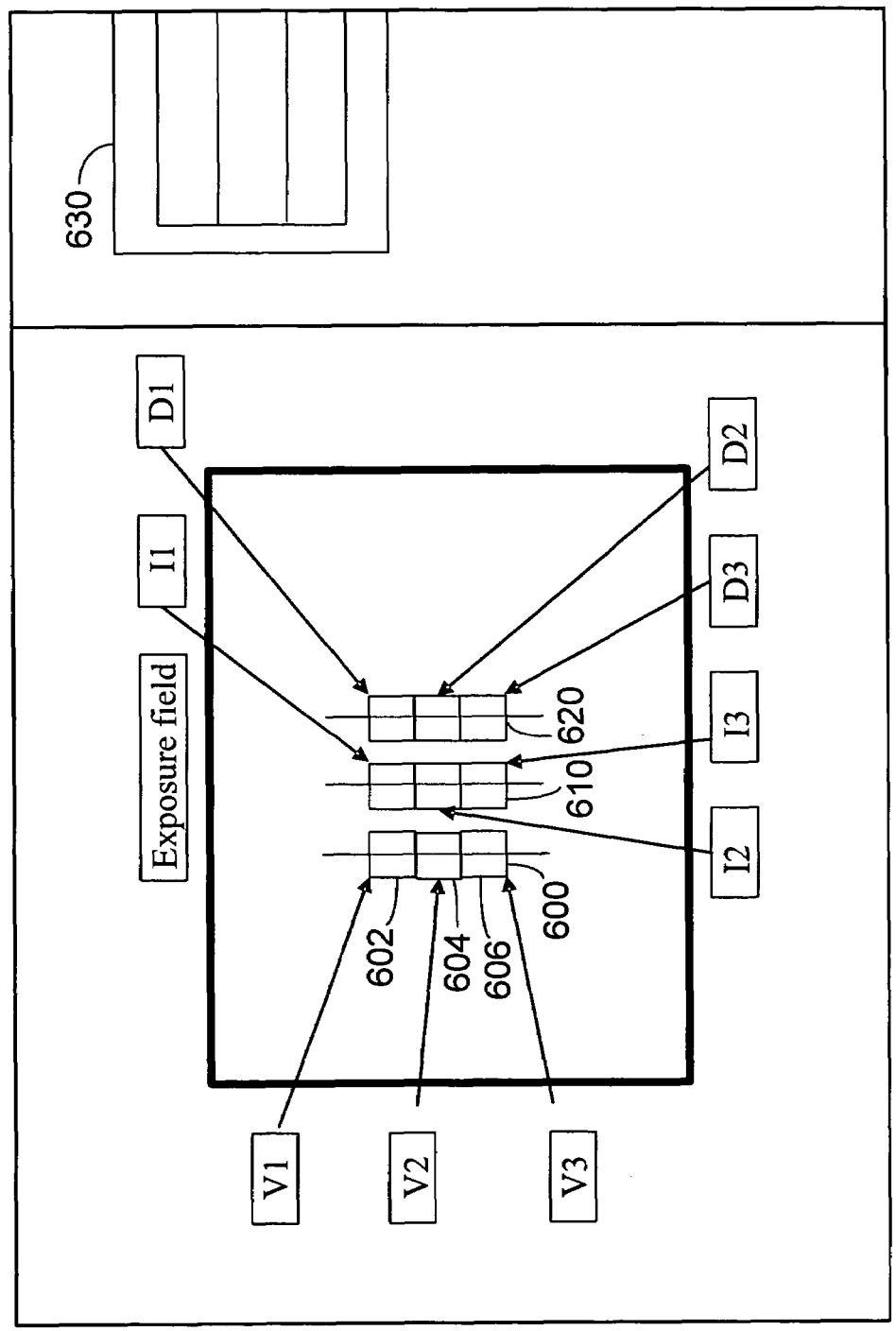
FIG. 6 is a plan view of a test region on a wafer according to an embodiment.

In an embodiment, a technique for characterizing and reducing shrinkage carryover due to CD-SEM measurements may include performing multiple measurements using varying CD-SEM conditions, e.g., voltage, probe current, and dose, on different parts of the same feature, as shown in FIG. 6. For example, the measurement at the upper portion 602 of a line feature 600 may be taken at a voltage V1, a mid portion 604 at a voltage V2, and a lower portion 606 at a voltage V3 (e.g., where V1<V2<V3), while maintaining the probe current at a current I1 for all three measurements. The three portions of the line feature may be completely separated or may have considerable overlaps. The resist shrinkage carryover may then be characterized as a function of beam voltage. Similarly, multiple measurements using varying probe currents (e.g., I1<I2<I3) may be performed on different portions of another line feature 610. Another set of measurements may be taken at varying dose of electron energy (e.g., D1<D2<D3) of another line feature 620. The three sets of measurements mentioned above can be performed on the same type of feature, such as a line, within the same exposure field.

Figure 7:
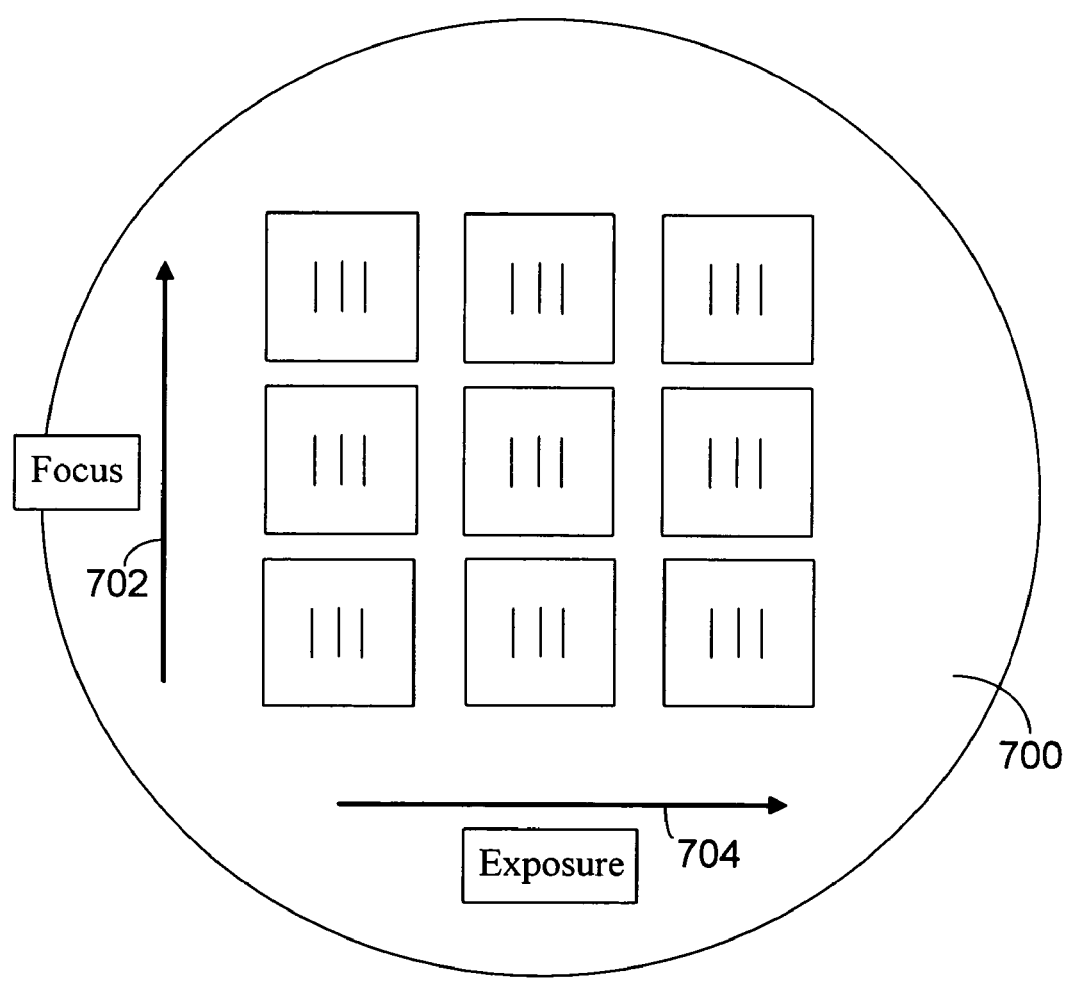
FIG. 7 is a plan view of a test region on a wafer according to another embodiment.

In an embodiment, measurements may be performed in a matrix of lithographic conditions, e.g., focus 702 and exposure 704, on a wafer 700, as shown in FIG. 7. The resist features may be printed under a range of focus and exposure settings, causing the resist profile to vary among the features in different fields. A characterization technique may be repeated in each field of interest for the characterization of the resist shrinkage carryover among different lithographic conditions.

The test features shown in FIGS. 6 and 7 may be provided in a scribe line of the wafer, or in the actual chips in unused regions 625 of one or more device layers. The features may be structurally similar to actual features in the chip (e.g., circuit components 630), but non-functional.

In an embodiment, substantially identical test features may be used to test and compare different CD-SEM tools. The amount of shrinkage carryover caused by the different CD-SEM tools at the same conditions may be compared for selection of a CD-SEM tool for a particular implementation.

Figure 8A:
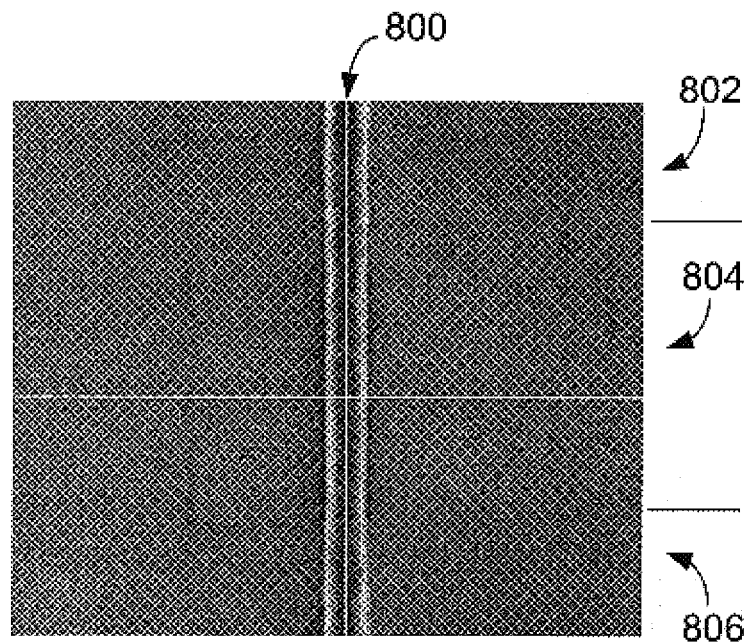
FIG. 8A is an image of a resist line having severe shrinkage or slimming effect due to CD-SEM measurement.

FIG. 8A shows shrinkage in a P8×5 193 nm resist line 800 due to measurement with an 800V CD-SEM beam voltage condition. The line includes an upper section 802, a middle section 804, and a lower section 806. A measurement in the middle section 804 causes the line to shrink by over 10% in the middle section 804. This corresponds to the slimming of the middle section 202 of the resist line shown in FIG. 2B.

Figure 8B:
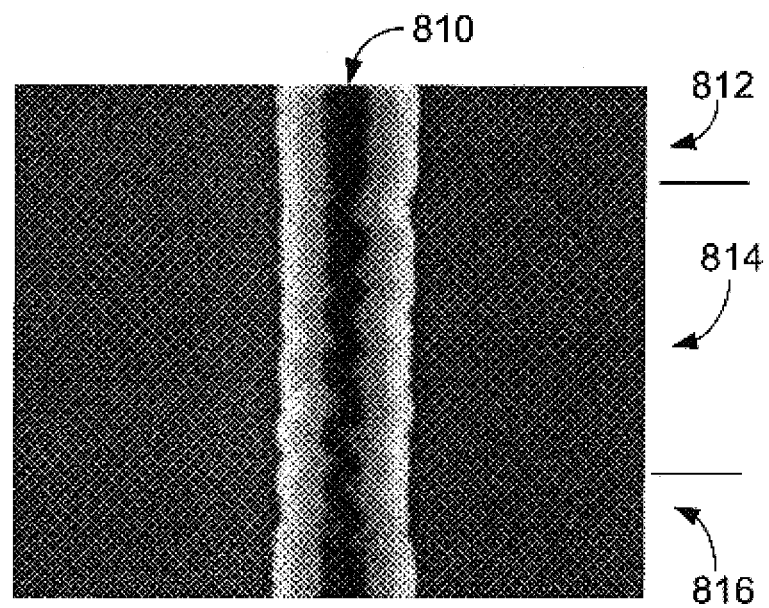
FIG. 8B is an image of a post-etch line pattern showing shrinkage carryover or fingerprint corresponding the shrunk resist line of FIG. 8A.

FIG. 8B shows the corresponding post-etch shrinkage fingerprint (i.e., shrinkage carryover) in the etched line 810, with upper section 812, middle section 814, and lower section 816. The magnitude of shrinkage carryover in the middle section 814 of the etched line in this case is greater than 15% compared with an unmeasured line. This corresponds to the thinned middle portion 204 of the etched line shown in FIG. 2C. The middle section 814 of the etched line in this case also exhibits line edge roughness, which may also be induced by an SEM measurement in the resist measurement step. Consequently, line edge roughness effects may also be reduced using the techniques described above.

Figure 9:
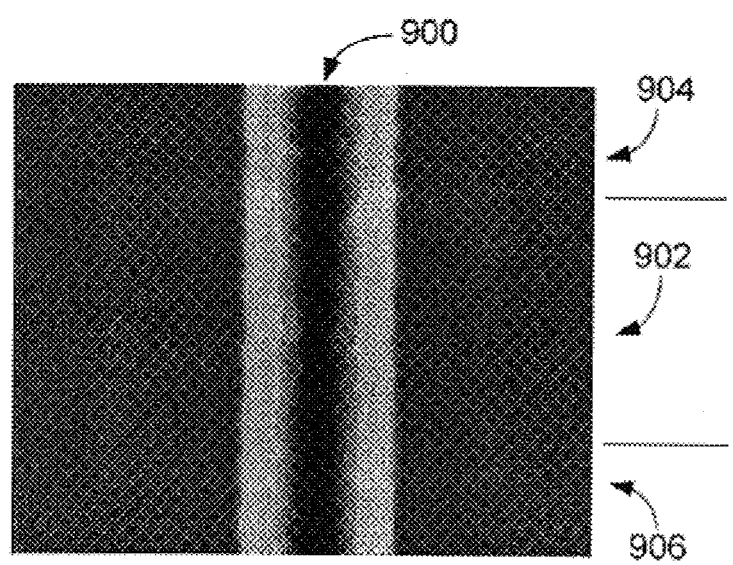
FIG. 9 is an image of a post-etch line pattern produced using a technique for reducing shrinkage carryover due to CD-SEM measurement according to an embodiment.

In comparison, a resist line feature measured with a lower beam voltage (400V) determined using an embodiment of the CD-SEM measurement produced a post-etch line 900 with significantly lower shrinkage carryover (less than 1% of the feature size in P8×5 process), as shown in FIG. 9. In this case, there is little, if any, variation between the average width of the middle section 902 of the etched line 900 compared to the upper section 904 and lower section 906.

A number of embodiments have been described. Nevertheless, it will be understood that various modifications may be made without departing from the spirit and scope of the invention. For example, blocks in the flowcharts may be skipped or performed out of order and still produce desirable results. Accordingly, other embodiments are within the scope of the following claims.

The invention claimed is:

1. A method comprising:
   measuring a first feature in a first resist layer with a scanning electron microscope using a first measurement condition;
   measuring a first etched feature in one or more device layers corresponding to the first feature in the first resist layer; and
   in response to identifying a shrinkage carryover in the first etched feature exceeding a threshold, selecting a second measurement condition different than the first measurement condition.

2. The method of claim 1, further comprising:
   measuring a second feature in a second resist layer with the scanning electron microscope using the second measurement condition.

3. The method of claim 2, further comprising:
   measuring a second etched feature in one or more device layers corresponding to the second feature in the second resist layer; and
   in response to identifying a shrinkage carryover in the second etched feature exceeding the threshold, selecting a third measurement condition different than the first measurement condition.

4. The method of claim 1, wherein said measuring using the first measurement condition comprises measuring using a set of parameters including a first voltage, and
   wherein said measuring using the second measurement condition comprises measuring using a set of parameters including a second voltage different than the first voltage.

5. The method of claim 1, wherein said measuring using the first measurement condition comprises measuring using a set of parameters including a first probe current, and
   wherein said measuring using the second measurement condition comprises measuring using a set of parameters including a second probe current different than the first probe current.

6. The method of claim 1, wherein said measuring using the first measurement condition comprises measuring using a set of parameters including a first dose of electron energy, and
   wherein said measuring using the second measurement condition comprises measuring using a set of parameters including a second dose of electron energy different than the first dose of electron energy.

7. The method of claim 1, wherein said measuring using the first measurement condition comprises measuring using a set of parameters including a first exposure, and
   wherein said measuring using the second measurement condition comprises measuring using a set of parameters including a second exposure different than the first exposure.

8. The method of claim 1, wherein said measuring using the first measurement condition comprises measuring using a set of parameters including a first focus condition, and
   wherein said measuring using the second measurement condition comprises measuring using a set of parameters including a second focus condition different than the first focus condition.

9. The method of claim 1, further comprising:
   measuring a second feature in the first resist layer with the scanning electron microscope using the second measurement condition.

10. The method of claim 1, wherein said measuring the first feature in the first resist layer comprises measuring a feature in a resist layer comprising a sub-193 nm resist material.

11. The method of claim 1, wherein said measuring the first etched feature comprises measuring the first etched feature using a third measurement condition, wherein the third measurement condition is not equal to the first measurement condition.

12. The method of claim 1, wherein said measuring the first feature comprises measuring the first feature at a measurement location on the first feature,
   wherein said measuring the first etched feature comprises measuring the first etched feature at a first location corresponding to the measurement location;
   and wherein said identifying the shrinkage carryover comprises:
   measuring the first etched feature at a second location corresponding to an unmeasured location on the first feature in the first resist layer; and
   comparing the measurements of the first etch feature at the first location and the second location.

13. The method of claim 1, wherein the first etched feature comprises a line, and
   wherein said identifying the shrinkage carryover comprises identifying a portion of the first etched feature that is narrower than another portion of the first etched feature.

14. The method of claim 1, wherein the first etched feature comprises a space, and
   wherein said identifying the shrinkage carryover comprises identifying a portion of the first etched feature that is wider than another portion of the first etched feature.

15. The method of claim 1, further comprising:
   measuring a test feature in a resist layer with another scanning electron microscope using the first measurement condition, the test feature having substantially similar dimensions and composition of the first feature;
   measuring a test etched feature in one or more device layers corresponding to the test feature in said resist layer;
   identifying a shrinkage carryover in the test etched feature; and
   comparing the shrinkage carryover identified in the first etched feature with the shrinkage carryover identified in the test etched feature.

16. An apparatus comprising:
   a scanning electron microscope to measure a first feature in a first resist layer using a first measurement condition and measure a first etched feature in one or more device layers corresponding to the first feature in the first resist layer; and
   an analysis module to comprising:
      a computation module to analyze the results of the measurement of the first etched feature to identify an amount of shrinkage carryover, and
      a selection module to select a second measurement condition in response different than the first measurement condition to the amount of shrinkage carryover exceeding a threshold.

17. The apparatus of claim 16, wherein the scanning electron microscope is further operative to measure a second feature in a second resist layer using the second measurement condition.

18. The apparatus of claim 17, wherein the scanning electron microscope is further operative to measure a second etched feature in one or more device layers corresponding to the second feature in the second resist layer, and
   wherein the selection module is operative to select a third measurement condition in response different than the first measurement condition to the computation module identifying a shrinkage in the second etched feature carryover exceeding the threshold.

19. The apparatus of claim 16, wherein the first measurement condition comprises a set of parameters including a first voltage, and wherein the second measurement condition comprises a set of parameters including a second voltage different than the first voltage.

20. The apparatus of claim 16, wherein the first measurement condition comprises a set of parameters including a first probe current, and wherein the second measurement condition comprises a set of parameters including a second probe current different than the first probe current.

21. The apparatus of claim 16, wherein the first measurement condition comprises a set of parameters including a first dose of electron energy, and wherein the second measurement condition comprises a set of parameters including a second dose of electron energy different than the first dose of electron energy.

22. The apparatus of claim 16, wherein the first measurement condition comprises a set of parameters including a first exposure, and wherein the second measurement condition comprises a set of parameters including a second exposure different than the first exposure.

23. The apparatus of claim 16, wherein the first measurement condition comprises a set of parameters including a first focus condition, and wherein the second measurement condition comprises a set of parameters including a second focus condition different than the first focus condition.

24. The apparatus of claim 16, wherein the scanning electron microscope is further operative to measure a second feature in the first resist layer using the second measurement condition different than the first measurement condition.

25. The apparatus of claim 16, wherein the first resist layer comprising a sub-193 nm resist material.

26. The apparatus of claim 16, wherein the scanning electron microscope is operative to measure the first etched feature using a third measurement condition, wherein the third measurement condition is not equal to the first measurement condition.

27. An article comprising a machine-readable medium comprising machine-executable instructions to cause one or more machines to:

control a scanning electron microscope to measure a first feature in a first resist layer using a first measurement condition;

control the scanning electron microscope to measure a first etched feature in one or more device layers corresponding to the first feature in the first resist layer;

identify a shrinkage carryover in the first etched feature exceeding a threshold; and select a second measurement condition different than the first measurement condition.

28. The article of claim 27, further comprising instructions to cause the one or more machines to:

control the scanning electron microscope to measure a second feature in a second resist layer using the second measurement condition.

29. The article of claim 28, further comprising instructions to cause the one or more machines to:

control the scanning electron microscope to measure a second etched feature in one or more device layers corresponding to the second feature in the second resist layer;

identify a shrinkage carryover in the second etched feature exceeding the threshold; and select a third measurement condition different than the first measurement condition.

30. The article of claim 27, wherein the first measurement condition comprises a set of parameters including a first voltage, and wherein the second measurement condition comprises a set of parameters including a second voltage different than the first voltage.

31. The article of claim 27, wherein the first measurement condition comprises a set of parameters including a first probe current, and wherein the second measurement condition comprises a set of parameters including a second probe current different than the first probe current.

32. The article of claim 27, wherein the first measurement condition comprises a set of parameters including a first dose of electron energy, and wherein the second measurement condition comprises a set of parameters including a second dose of electron energy different than the first dose of electron energy.

33. The article of claim 27, wherein the first measurement condition comprises a set of parameters including a first exposure, and wherein the second measurement condition comprises a set of parameters including a second exposure different than the first exposure.

34. The article of claim 27, wherein the first measurement condition comprises a set of parameters including a first focus condition, and wherein the second measurement condition comprises a set of parameters including a second focus condition different than the first focus condition.

35. The article of claim 27, further comprising instructions to cause the one or more machines to:

control the scanning electron microscope to measure a second feature in the first resist layer using the second measurement condition different than the first measurement condition.

36. The article of claim 27, wherein the first resist layer comprises a sub-193 nm resist material.

37. The article of claim 27, wherein the instructions to control the scanning electron microscope to measure the first etched feature comprise instructions to control the scanning electron microscope to measure the first etched feature using a third measurement condition, wherein the third measurement condition is not equal to the first measurement condition.

38. A method comprising:

measuring a first feature in a first resist layer with a scanning electron microscope using a first measurement condition;

measuring a first etched feature in one or more device layers corresponding to the first feature in the first resist layer; and in response to identifying an edge roughness in the first etched feature exceeding a threshold, selecting a second measurement condition different than the first measurement condition.

39. The method of claim 38, further comprising:

measuring a second feature in a second resist layer with the scanning electron microscope using the second measurement condition.

* * * * *